United States Patent [19]

Kruger

[11] Patent Number: 4,552,582
[45] Date of Patent: Nov. 12, 1985

[54] COTTON DEFOLIANT COMPOSITIONS
[75] Inventor: Paul J. Kruger, Middlesex, N.J.
[73] Assignee: J. T. Baker Chemical Co., Phillipsburg, N.J.
[21] Appl. No.: 517,424
[22] Filed: Jul. 28, 1983

Related U.S. Application Data

[63] Continuation-in-part of Ser. No. 412,144, Aug. 27, 1982, abandoned.

[51] Int. Cl.$^4$ ............................................. A01N 43/82
[52] U.S. Cl. .......................................... 71/73; 71/65; 71/69; 71/81; 71/90
[58] Field of Search ................... 71/73, 65, 69, 81, 90

[56] References Cited

U.S. PATENT DOCUMENTS 2,368,601  1/1945  Torley ...................................... 71/69
4,261,729  4/1981  Rush et al. ............................... 71/73
4,294,605  10/1981 Arndt et al. .............................. 71/73

FOREIGN PATENT DOCUMENTS 1118226  2/1982  Canada .

OTHER PUBLICATIONS

EPA. Chem. Abst., vol. 95, (1981), 78636t.
Stephenson, Chem. Abst., vol. 96, (1982), 47577r.
Rozhkova, Chem. Abst., vol. 85, (1976), 187622z.

*Primary Examiner*—Catherine L. Mills
*Attorney, Agent, or Firm*—George W. Rauchfuss, Jr.

[57] ABSTRACT

An improved cotton defoliant formulation comprising a mixture of thidiazuron and an effective potentiating amount of an ammonium, quaternary alkyl ammonium, alkali metal or alkaline earth metal thiocyanate.

10 Claims, No Drawings

COTTON DEFOLIANT COMPOSITIONS

CROSS REFERENCE TO RELATED APPLICATION

This application is a continuation-in-part of my co-pending application Ser. No. 412,144, filed Aug. 27, 1982 abandoned.

FIELD OF THE INVENTION

The invention relates to enhancing the cotton defoliating activity of thidiazuron by certain thiocyanates.

BACKGROUND OF THE INVENTION

Thidiazuron, the common name for N-phenyl-N'-1,2,3-thiadiazol-5-ylurea, is a known cotton defoliant and has been registered for such purpose with the Environmental Protection Agency (EPA). Thiocyanates, in general, have found several agricultural applications such as herbicides, crop desiccants, and defoliants, adjuvants and the like. For example, the cotton defoliant activity of ammonium and alkali metal thiocyantes, is shown in U.S. Pat. No. 2,368,601, issued Jan. 30, 1945 to Robt. E. Torley and assigned to American Cyanamid Company.

In some cases, active agricultural chemicals have been shown to be more effective in combination than when applied individually. The result is often termed "potentiation" or "synergism" since the combination demonstrates a potency or activity level exceeding that which it would be expected to have, based on a knowledge of the individual potencies of the components.

The present invention resides in the discovery that the cotton defoliating activity of thidiazuron is markedly enhanced when used in combination with certain thiocyanates, particularly ammonium thiocyante.

DETAILED DESCRIPTION OF THE INVENTION

It has now been found that synergism in the defoliation of cotton is exhibited by thidiazuron and a thiocyanate compound selected from the group consisting of ammonium, quaternary alkyl ammonium, alkali metal and alkaline earth metal thiocyante. In addition to ammonium thiocyante, other thiocyantes that may be employed are, for example, alkali metal thiocyanates, such as sodium and potassium thiocyanate, alkaline earth metal thiocyanates such as magnesium and calcium thiocyanate, and quaternary alkyl ammonium thiocyanates such as trialkyl and tetraalkyl ammonium thiocyanates, e.g., trimethyl dodecyl ammonium thoiocyanate and the like. The preferred thiocyanates are ammonium, sodium and potassium thiocyanate, ammonium thiocyanate being most preferred.

A particularly suitable aqueous formulation of ammonium thiocyanate for use herein is the commercial product registered with the Environmental Protection Agency (EPA) as a spray adjuvant and available under the trade name "Intensify" from the J. T. Baker Chemical Co. This product is a flowable formulation consisting of an aluminum hydroxide gel suspension of ammonium thiocyanate containing about 44.5% ammonium thiocyanate.

Thidiazuron, chemically known as N-phenyl-N'-1,2,3-thiadiazol-5-ylurea, is registered with the Environmental Protection Agency EPA as a cotton defoliant. It is the active ingredient (A.I.) in, and is commercially available as, a 50% w/w wettable powder under the trade name "Dropp" from Nor-Am Agricultural Products, Inc. The EPA-approved dosage of Dropp ranges from 0.2 to 0.4 pound per acre (equivalent to 0.1 to 0.2 lb/acre A.I.) with a maximum of 0.6 pound per acre (equivalent to 0.3 lb/acre A.I.) for two applications.

According to this invention, the cotton defoliating activity of thidiazuron is markedly potentiated by the aforementioned thiocyanates. Accordingly, application rates from as little as about 0.006 to about 0.4 lb/acre, preferably from about 0.006 to about 0.2 lb/acre, and most preferably from about 0.06 to about 0.1 lb/acre, of thidiazuron can now be utilized in conjunction with an effective cotton defoliation potentiating amount of said thiocyanates, in general, at least about 1 lb/acre, and, preferably, from about 2 to about 8 lbs/acre. However, based on economic factors, it is most preferred to use from about 2 to about 4 lbs/acre of said thiocyanates. The aforementioned application rates of thidiazuron (0.1–0.3 lb/acre) to effectively defoliate cotton may be substantially reduced when used in conjunction with said thiocyanates as herein described.

In the cotton defoliating compositions of the invention, the thiocyanate:thidiazuron weight ratio at which the cotton defoliating response is synergistic generally lies within the range of from about 5:1 to about 1335:1, preferably, from about 10:1 to about 1335:1, and most preferably from about 20:1 to about 670:1. For spraying purposes, both ingredients are generally dispersed or suspended in a sufficient amount of water or a vegetable oil such as soybean oil, cottonseed oil and the like to give complete and uniform coverage of the cotton foliage and the spray mix can be advantageously applied by air or by ground equipment. Although it is convenient to apply both thidiazuron and thiocyanate components simultaneously in one formulation, each can be applied substantially simultaneously in separate formulations with the effect of a combined application.

The compositions according to the invention are obtained in known manner by intimately mixing and/or grinding the two synergistic components with suitable inert carriers, with or without the addition of dispersants, suspending agents or solvents which are inert toward the active components. Pre-mix concentrates such as, for example, wettable powders, slurries and suspendible liquid concentrates wherein the concentration of active components may range from about 10 to about 90 percent by weight, are advantageous for storing purposes. When required for use, simple admixture of the pre-mix concentrate with a suitable diluent to the desired application dosage is all that is necessary.

Advantageous compositions for spraying purposes are aqueous mixes containing, per gallon of composition, from about 0.00075 to about 0.8 pound, preferably from about 0.00075 to about 0.4 pound, and most preferably from about 0.0015 to about 0.2 pound of thidiazuron in combination with from about 1 to about 4 pounds of thiocyanate compound. In preparing tank mixes, a gallon of such composition may be diluted with from about 2 to about 10 gallons of water for aerial spraying and from about 10 to about 30 gallons of water for ground spraying equipment.

Formulations will generally contain one or more surface active agents to promote rapid dispersion of the two synergistic components in aqueous medium to form stable, sprayable suspensions. The surface active agent is generally employed in an amount of from about 0.1 to about 6 percent by weight based on the weight of the total formulation. The term "surface active agent" is understood to include surfactants, wetting agents, dispersing agents, emulsifying agents and the like. Such surface active agents, including those suitable for agricultural applications, are well known and reference is made to U.S. Pat. No. 2,547,724, Columns 3 and 4, for detailed examples of same. Non-ionic surface active agents are preferred and particularly suitable is the non-ionic surfactant commercially available under the trade name "Ortho X-77" from the Chevron Chemical Co., the principal functioning agents of which are alkylarylpolyoxyethylene glycols, free fatty acids and isopropanol.

Examples of suitable wetting and dispersing agents are non-ionic aromatic polyethylene glycol ethers, such as Antarox A-400, alkyl aryl polyether alcohol type emulsifiers such as Triton X-100, sulfonated purified lignins such as Reax 45A and 45L.

The formulations of active ingredients dissolved in water can contain one or more of any suitable suspending agents, such as for example, methylcellulose, hydroxypropylmethylcellulose, magnesium hydroxide gel, bentonite, Veegum, attapulgite clays, hydroxypropyl guar, aluminum hydroxide gel and the like. The suspending agents will generally be employed in an amount of from about 5 to about 30% by weight based on the weight of the total formulation, and preferably in an amount of from about 15 to about 25% by weight. Aluminum hydroxide gel containing about 2 to about 20% by weight, preferably from about 4 to about 10% by weight, aluminum hydroxide is employed as the preferred suspending agent for the formulations of this invention.

Any suitable freeze thaw agent can also be employed in the formulations of this invention, if desired, and is generally present in an amount of from about 1 to about 10% by weight based on the weight of the total formulation. Among such suitable freeze thaw agents there can be mentioned, for example, urea, polyhydric alcohols such as glycerol, sorbitol, mannitol, ethylene glycol, propylene glycol, polyethylene glycol, glucose, sucrose and the like as well as water soluble non-toxic polymeric agents such as dextran, polyvinylpyrrolidone and the like. Preferred for use in the formulations of this invention is propylene glycol.

Suitable antifoam agents may also be employed, if desired, and when employed are used in an amount of from about 0.1 to about 0.5% by weight based on the total weight of the formulation. Any suitable antifoam agent can be employed such as, for example a 50% by weight solution of 2,4,7,9-tetramethyl-5-decyn-4,7-diol known as Surfynol 104-E.

If desired, the formulations of this invention can also have present other additional substances such as herbicides, pesticides, insecticides, nematocides, fungicides, and the like; stabilizers, spreaders, deactivators, adhering agents, fertilizers and the like; and other defoliants, desiccants, plant growth regulants and the like.

The following examples provide further illustrations demonstrating the enhanced cotton defoliating response obtained from application of the two synergistic components.

EXAMPLE I

This example demonstrates the synergistic response of thidiazuron (N-phenyl-N'-1,2,3-thiadiazol-5-ylurea) and ammonium thiocyanate in combined application to cotton plants.

The thidiazuron was utilized as the commercial product, Dropp, a 50% wettable powder. This was diluted to the indicated concentrations using deionized water containing 0.125% v/v of the non-ionic surfactant, Ortho X-77. The ammonium thiocyanate was A.C.S. reagent grade and was also diluted to the indicated concentrations using water containing 0.125% v/v of Ortho X-77.

Plastic pots measuring $25 \times 25$ cm were filled to a depth of 20 cm with growing medium containing sphagnum peat moss, horticultural vermiculite, processed bark, composted pine bark and washed granite sand. Each pot was seeded with five Deltapine 61 cotton (*Gossypium hirsutum*) seeds. The pots were placed in a greenhouse and watered regularly. After 3 weeks the plants were thinned to three per pot.

At an age of 3 to 3.5 months, the number of leaves on the plants in each pot was counted. Then the plants were sprayed with aqueous formulations of the test compounds. The quantities sprayed were such that the amount of each test compound applied per pot corresponded to the desired application rate in pound(s) per acre. In control pots the test compounds were applied alone at various application rates, whereas in the test pots, solutions containing both compounds were applied.

Seven and fourteen days later, the leaves were again counted and percent defoliation calculated as follows:

$$\% \text{ Defoliation} = 100 - \left( \frac{\text{Number of leaves on post-treatment day}}{\text{Number of leaves before treatment}} \times 100 \right)$$

The results of this test are listed in Table I in the columns headed by the symbol "O" (indicating the "observed" results). These results are compared with the expected results, shown in the columns headed by the symbol "E", derived from the control data using Limpel's formula (Limpel et al, 1962 "Weed Control by Dimethylchloroterephthalate Alone and in Certain Combinations," Proc. NEWCC., Vol. 16, pp. 48-53):

$$E = X + Y - XY/100$$

where:
 X=observed percent activity when one of the compounds is used alone, and
 Y=observed percent activity when the other compound is used alone.

An asterisk (*) is used to indicate the tests where the results show synergism, i.e., where the observed result exceeds the expected result. It is clear from the table that synergism was observed at many of the application rates tested.

TABLE I

Defoliant Synergism Test Results
Test Compounds:
A: Thidiazuron
B: Ammonium Thiocyanate
Applied To Cotton Plants
Percent Defoliation - O: Observed, E: Expected

| Application Rates (lb/acre) | | 7 Days | | 14 Days | |
|---|---|---|---|---|---|
| A | B | O | E | O | E |
| Control Data: | | | | | |
| .006 | — | 41 | | 54 | |
| .012 | — | 52 | | 68 | |
| .024 | — | 68 | | 82 | |
| .05 | — | 48 | | 98 | |
| .1 | — | 84 | | 100 | |
| .4 | — | 73 | | 100 | |
| — | 2 | 0 | | 5 | |
| — | 4 | 13 | | 13 | |
| — | 8 | 3 | | 10 | |
| Test Data: | | | | | |
| .006 | 4 | 49 | 49 | 70* | 60 |
| .012 | 2 | 43 | 52 | 75* | 70 |
| .012 | 4 | 54 | 58 | 77* | 72 |
| .012 | 8 | 62* | 53 | 87* | 71 |
| .024 | 4 | 87* | 72 | 100* | 84 |
| .05 | 2 | 73* | 48 | 99* | 98 |
| .05 | 4 | 75* | 54 | 99* | 98 |
| .05 | 8 | 86* | 50 | 99* | 98 |
| .1 | 4 | 80 | 86 | | |
| .4 | 4 | 70 | 76 | | |

*Synergistic effect shown

Blank spaces in the Test Data indicate 100% defoliation in both observed and expected results, precluding evaluation of synergism.

EXAMPLE II

This example represents a repeat of the test shown in Example I with alternate formulations. The thidiazuron was utilized as the Dropp 50% wettable powder and was diluted using deionized water. Ammonium thiocyanate was utilized as the Intensify flowable formulation containing 4 lb/gal of ammonium thiocyanate and was diluted using deionized water.

TABLE II

Defoliant Synergism Test Results
A: Thidiazuron
B: Ammonium Thiocyanate
Applied to Cotton Plants
Percent Defoliation - O: Observed, E: Expected

| Application Rates (lb/acre) | | 7 Days | | 14 Days | |
|---|---|---|---|---|---|
| A | B | O | E | O | E |
| Control Data: | | | | | |
| .05 | — | 88 | | 98 | |
| .1 | — | 88 | | 94 | |
| .2 | — | 96 | | 99 | |
| .4 | — | 91 | | 98 | |
| — | 4 | 19 | | 25 | |
| Test Data: | | | | | |
| .05 | 4 | 100* | 90 | 100* | 98 |
| .1 | 4 | 100* | 90 | 100* | 98 |
| .2 | 4 | 100* | 97 | 100* | 99 |
| .4 | 4 | 100* | 93 | 100* | 98 |

*Synergistic effect shown

EXAMPLE III

This example demonstrates the utility of combined thidiazuron and ammonium thiocyanate applications to field-grown cotton. The formulation utilized were the same as in Example II.

Cotton (variety Lankart 57) was planted in test plots measuring 12.7×40 ft in Houston Black Clay soil located in Hutto, Texas (Williamson County).

At an age of five months, the number of leaves on five consecutive plants in each of two center rows in each test plot were counted. Then these center rows were sprayed with aqueous formulations of the test compounds. The quantities sprayed were such that the amount of each test compound applied corresponded to the desired application rate in pounds per acre. Five and ten days later the leaves were again counted and percent defoliation calculated as in Example I.

The results of this test are listed in Table III.

TABLE III

Field Defoliation Test Results
Test Compounds:
A: Thidiazuron
B: Ammonium Thiocyanate
Applied to Field-Grown Cotton Plants

| Application Rates (lb/acre) | | Percent Defoliation | |
|---|---|---|---|
| A | B | 5 Days | 10 Days |
| .2 | — | 38 | 67 |
| .1 | 2 | 40 | 68 |

This data indicates that the amount of Compound A can be reduced by one-half without affecting percent defoliation if Compound B is added. Enhancement of the cotton defoliant activity of Compound A is clearly indicated.

EXAMPLE IV

This sample demonstrates the synergistic response of thidiazuron and ammonium thiocyanate in combined application to cotton in large field plots.

Cotton (variety D&PL55) was planted in test plots measuring 6 rows×400 ft. at College Station, Texas. At an age of five months the plants were sprayed with aqueous formulations of the test compounds. The thidiazuron was utilized as the Dropp 50% wettable powder and the ammonium thiocyanate was utilized as the Intensify flowable formulation containing 4 lb/gal of ammonium thiocyanate. Each of the test compounds was diluted with water to provide the application rates indicated below. Seven and fourteen days later the plots were visually rated for percent defoliation. Synergism was calculated as in Example I and the results displayed in Table IV. Synergism was observed for every rate used.

TABLE IV

Defoliant Synergism Test Results
Test Compounds:
A: Thidiazuron
B: Ammonium Thiocyanate
Applied to Cotton Plants
Percent Defoliation - O: Observed, E: Expected

| Application Rates (lb/acre) | | 7 Days | | 14 Days | |
|---|---|---|---|---|---|
| A | B | O | E | O | E |
| Control Data: | | | | | |
| .0125 | — | 10 | | 20 | |
| .025 | — | 10 | | 25 | |
| .05 | — | 20 | | 30 | |
| .10 | — | 60 | | 90 | |
| — | 2 | 0 | | 0 | |
| Test Data: | | | | | |
| .0125 | 2 | 25* | 10 | 30* | 20 |
| .025 | 2 | 25* | 10 | 35* | 25 |
| .05 | 2 | 30* | 20 | 60* | 30 |

TABLE IV-continued

Defoliant Synergism Test Results
Test Compounds:
A: Thidiazuron
B: Ammonium Thiocyanate
Applied to Cotton Plants
Percent Defoliation - O: Observed, E: Expected

| Application Rates (lb/acre) | | 7 Days | | 14 Days | |
|---|---|---|---|---|---|
| A | B | O | E | O | E |
| .10 | 2 | 90* | 60 | 100* | 90 |

*Synergistic effect shown.

EXAMPLE V

This example demonstrates the synergistic response of thidiazuron with two additional thiocyanate salts, sodium thiocyanate and potassium thiocyanate.

The thidiazuron was utilized as the commercial product, Dropp, which was diluted to the indicated concentrations using deionized water containing 0.25% v/v of the non-ionic surfactant, Ortho X-77. The sodium and potassium thiocyanate were both reagent grade and were also diluted to the indicated concentrations using deionized water containing 0.25% v/v of Ortho X-77.

The experimental procedure was the same as for Example I. It is clear from Table V that synergism was observed at the rates tested.

TABLE V

Defoliant Synergism Test Results
Test Compounds:
A: Thidiazuron
B: Sodium Thiocyanate
C: Potassium Thiocyanate
Applied to Cotton Plants
Percent Defoliation - O: Observed, E: Expected

| Application Rates (lb/acre) | | | 7 Days | | 14 Days | |
|---|---|---|---|---|---|---|
| A | B | C | O | E | O | E |
| Control Data: | | | | | | |
| .025 | — | — | 18 | | 56 | |
| — | 8 | — | 3 | | 15 | |
| — | — | .8 | 8 | | 10 | |
| Test Data: | | | | | | |
| .025 | 8 | — | 64* | 20 | 82* | 63 |
| .025 | — | 8 | 45* | 24 | 78* | 60 |

*Synergistic effect shown.

EXAMPLE VI

This example demonstrates the synergistic response of thiazuron with ammonium thiocyanate when applied to "rank" cotton plants. "Rank" is a term applied to field cotton when the ground is moist and the cotton is actively growing. "Rankness" is occasionally encountered at harvesting (defoliation) time.

Thidiazuron was utilized as in Example V. Ammonium thocyanate was ACS reagent grade and was diluted to the indicated concentrations using water containing 0.25% v/v of Ortho X-77.

The experimental procedure was similar to that of Example I using 2.5 month old Delta Pine 55 cotton plants. Watering was continued throughout the defoliation period to assure "rankness". It is clear from Table VI that synergism was observed at all rates tested.

TABLE VI

Defoliant Synergism Test Results
Test Compounds:
A: Thidiazuron
B: Ammonium Thiocyanate
Applied to Cotton Plants
Percent Defoliation - O: Observed, E: Expected

| Application Rates (lb/acre) | | 7 Days | | 10 Days | |
|---|---|---|---|---|---|
| A | B | O | E | O | E |
| Control Data: | | | | | |
| 0.1 | — | 14 | | 44 | |
| 0.2 | — | 24 | | 71 | |
| — | 2 | 0 | | 0 | |
| — | 4 | 0 | | 0 | |
| Test Data: | | | | | |
| 0.1 | 2 | 20* | 14 | 60* | 44 |
| 0.1 | 4 | 29* | 14 | 83* | 44 |
| 0.2 | 2 | 30* | 24 | 80* | 71 |
| 0.2 | 4 | 37* | 24 | 81* | 71 |

*Synergistic effect shown.

EXAMPLE VII

This example demonstrates the synergistic response of thidiazuron with sodium thiocyanate and potassium thiocyanate when applied to "rank" cotton plants.

Test compounds were utilized as in Example V. The experimental procedure was similar to that of Example VI. It is clear from Table VII that synergism was observed at the rates tested.

TABLE VII

Defoliant Synergism Test Results
Test Compounds:
A: Thidiazuron
B: Sodium Thiocyanate
C: Potassium Thiocyanate
Applied to Cotton Plants
Percent Defoliation - O: Observed, E: Expected

| Application Rates (lb/acre) | | | 7 Days | | 10 Days | |
|---|---|---|---|---|---|---|
| A | B | C | O | E | O | E |
| Control Data: | | | | | | |
| 0.2 | — | — | 86 | | 88 | |
| — | 4 | — | 0 | | 0 | |
| — | — | 4 | 0 | | 0 | |
| Test Data: | | | | | | |
| 0.2 | 4 | — | 92* | 86 | 96* | 88 |
| 0.2 | — | 4 | 88* | 86 | 94* | 88 |

*Synergistic effect shown.

I claim:

1. A cotton defoliant composition consisting essentially of an effective cotton defoliating mixture of thidiazuron and a thiocyanate compound as a cotton defoliating potentiating agent, the weight ratio of thiocyanate compound to thidiazuron being from about 10:1 to about 640:1 and said thiocyanate compound is selected from the group consisting of ammonium thiocyanate, sodium thiocyanate and potassium thiocyanate.

2. A cotton defoliant composition of claim 1 wherein said thiocyanate compound is ammonium thiocyanate.

3. A cotton defoliant composition of claim 2 wherein the ratio of ammonium thiocyanate to thidiazuron is from about 20:1 to about 320:1.

4. A cotton defoliant composition of claim 2 wherein the ratio of ammonium thiocyanate to thidiazuron is from about 40:1 to about 160:1.

5. An aqueous cotton defoliant composition of claim 2 wherein thidiazuron is present in an amount from about 0.0075 to about 0.2 pound and the ammonium thiocyanate is present in an amount of from about 1 to about 4 pounds per gallon of composition.

6. A method of defoliating cotton comprising applying to cotton foliage an effective cotton defoliating amount of thidiazuron and an effective cotton defoliation potentiating amount of a thiocyanate compound selected from the group consisting of ammonium thiocyanate, sodium thiocyanate and potassium thiocyanate and wherein the ratio of thiocyanate compound to thidiazuron is from about 10:1 to about 640:1.

7. A method of defoliating cotton comprising applying to cotton foliage an effective cotton defoliating amount of a composition of claim 2.

8. A method of defoliating cotton comprising applying to cotton foliage an effective cotton defoliating amount of a composition of claim 3.

9. A method of defoliating cotton comprising applying to cotton foliage an effective cotton defoliating amount of a composition of claim 4.

10. A method of defoliating cotton comprising applying to cotton foliage an effective cotton defoliating amount of a composition of claim 5.

* * * * *